(12) United States Patent
Lamping et al.

(10) Patent No.: US 6,485,448 B2
(45) Date of Patent: Nov. 26, 2002

(54) KNEE STRAP

(75) Inventors: Cindy Lamping, Cincinnati, OH (US); Sherry Hinds, Goshen, OH (US); Suzanne Mernyk, Stamford, CT (US)

(73) Assignee: Beiersdorf Inc., Wilton, CT (US)

( * ) Notice: Subject to any disclaimer, the term of this patent is extended or adjusted under 35 U.S.C. 154(b) by 0 days.

(21) Appl. No.: 09/769,054

(22) Filed: Jan. 25, 2001

(65) Prior Publication Data

US 2002/0099314 A1 Jul. 25, 2002

(51) Int. Cl.[7] .................................................. A61F 5/00
(52) U.S. Cl. ................................ 602/26; 602/1; 602/23
(58) Field of Search ........................... 602/1, 5, 23, 26, 602/60–63

(56) References Cited

U.S. PATENT DOCUMENTS

| | | | | |
|---|---|---|---|---|
| 4,334,528 A | * | 6/1982 | Gauvry | 602/26 |
| 4,688,572 A | * | 8/1987 | Hubbard et al. | 607/112 |
| 5,417,647 A | * | 5/1995 | Down | 602/26 |
| 6,080,124 A | * | 6/2000 | Falk et al. | 602/26 |

* cited by examiner

Primary Examiner—Michael A. Brown
Assistant Examiner—Lalita M. Hamilton
(74) Attorney, Agent, or Firm—Norris McLaughlin & Marcus

(57) ABSTRACT

A knee strap comprised of an elongated flexible member having a tubular member secured to one surface thereof in a cloth pouch, a buckle on one end of the strap which cooperates with the other end of the strap to secure the strap around a human leg, the tubular member being positioned to enable the tubular member to bear immediately below the patella while the buckle bears on the side of the knee, and not the front or back.

7 Claims, 2 Drawing Sheets

KNEE STRAP

FIELD OF THE INVENTION

The present invention relates in general to flexible knee straps which are easy to apply, comfortable to wear and which are useful for treating disorders of the knee.

BACKGROUND OF THE INVENTION

Millions of people suffer from knee pain everyday due to conditions such as patellar tendinitis, arthritis, chondromalacia, synovitis, sprained or twisted joints and the like. There have been a number of knee braces and straps devised to relieve symptoms from such conditions.

U.S. Pat. No. 4,334,528, issued Jun. 15, 1982, and Design Patent 265,590 issued Jul. 27, 1982, describe a knee strap for aiding in the alignment of a patient's patella for reducing trauma on the undersurface of the patella. The strap comprises a flexible fabric strap member which encircles a person's leg immediately below the patella and a pair of end portions having hook and loop fasteners. The center portion of the strap is comprised of a tubular portion which itself is comprised of part of the fabric strap member and a compressible tubular member. The center portion of the strap is more rigid than the end portions and has a diameter which is less than the height of the end portions.

In use, the strap is placed immediately below the patella so that the center portion is positioned just beneath the kneecap. The end portions are wrapped around the leg behind the knee and are fastened with the hook and loop fastener. The portion of the strap that fastens behind the knee is flat and wider than the front portion. The construction is such that, when the knee is bent, the connecting means compress against the back of the knee which creates discomfort to the wearer. It can also potentially cause restriction in the flow of blood to the lower extremity and hamper the venous blood flow out of the lower extremity. Moreover, since the portion of the strap that fastens behind the knee is flat and is wider than the front portion, the adjustable range of the circumference is limited. Thus, the strap would not be suitable for use on an individual having a smaller sized extremity such as on a child or small adult, and would not be suitable for use on an arm.

U.S. Pat. No. 4,777,946 describes a therapeutic apparatus to be worn on the leg for the protection of the patella, for the correction of patellar maladies, and for the relief of pain associated with such maladies.

The device is comprised of an elastic patellar fixing member having front and rear surfaces with an opening positioned to fit over the patella. A belt extends from the fixing member and is secured around the knee joint. A pressing band overlies the front surface of the patellar fixing member and the opening and extends along the connecting belt. A patella pressing patch is located on the rear surface of the pressing band and is positioned lateral to the patella fixing member opening. In use, the device is positioned so that the connecting belt is secured around the knee joint.

U.S. Pat. No. 5,120,300 describes a compression band having preassembled male and female connectors.

U.S. Pat. No. 5,338,290 describes an elastic variable tension medical device and method for its use. The device comprises at least two elastic bands stacked one on top of another to form a stack of elastic bands. Reinforcing ribs are attached to the stack of elastic bands. Hook and loop fasteners are attached to each end of the elastic band stack.

U.S. Pat. No. 5,613,943 describes a patellar brace and method for its use. The patellar brace includes an elastic sleeve having an aperture for the knee and a strap assembly to which elastic arm members and a patellar bracing pad are attached. The patellar bracing pad is allowed to float with movement of the knee and is dynamically repositioned, depending on the amount of flexion and movement of the knee.

U.S. Pat. No. 5,865,782 describes a device and method for treating symptoms associated with inflamed soft tissue of the knee. The device comprises a planar, semi-rigid elastically deformable compression plate having a concave posterior surface. The device is adapted to fit between the tibial tuberosity and patella of the knee.

U.S. Pat. No. Des. 307,054 is directed to a patella brace. The brace is shown to have a removable member which is to be positioned against the knee.

In general, prior art knee straps to treat problems associated with flexion and extension of the knee are directed toward stabilizing, splinting or compressing the patella to prevent the lateral displacement of the patella during activity. The present invention provides a novel knee strap for treating common disorders of the knee which does not apply pressure to the patella and which is designed to minimize discomfort to the user and to minimize restriction of blood to the lower extremity.

SUMMARY OF THE INVENTION

The present invention is directed to a knee strap comprising an elongated flexible generally flat member, optionally having a first fabric covering bonded or otherwise attached to one side thereof and a second covering bonded or otherwise attached to the second side thereof, wherein the member has a length at least as long as the circumference of a human patient's leg at a point immediately below the patella so that the strap can be wrapped around the leg, and wherein the strap has a first end and a second end, a tubular member positioned on the strap in an orientation that is offset to the left or right of the midpoint of the length of the strap, and wherein the tubular member is encased within a cloth pouch affixed to one surface of the strap, wherein the ends of the strap are provided with at least one fastener, which cooperates with the second end of the strap to adjustably tighten and secure the strap around the side of a person's leg and wherein the strap is adapted so that, when in position around the leg if a human patient, the tubular portion bears against the front of the leg, below the patella and at least one fastener engages the other end of the strap at a position on one side of the patient's knee, and not at the front or back of the knee.

In use, the ends of the strap are fastened to each other such that the tubular member lies immediately beneath the patella and the adjustable strap fasteners are situated to sit on the side of the knee, not in front of or behind the knee.

BRIEF DESCRIPTION OF THE DRAWINGS

For the purposes of illustrating the invention, there is shown in the accompanying drawings one form of the present invention.

As shown in FIG. 2, the knee strap (1) of the present invention is comprised of an elongated first flexible fabric member (2) which has bonded to it a second flexible member (3) which comprises a material having a hook-engagable pile such as, for example, the loop portion of a hook and loop fastening system or other material capable of engaging the hook portion of a hook and loop fastening system One end of the knee strap is provided with a buckle (4), which is preferably concave in shape and has a loop sized to accommodate the other end of the strap, and the other end is provided with a tongue (5) secured to which is a hook material or fabric (6), such as the hook portion of a hook and loop fastening system, which, in a closed position, is passed through the loop of the buckle and looped back over itself to engage and cooperate with the material having the hook engagable pile (3) to releasably and adjustably hold the strap in a closed position around a human knee, as shown in FIG. 6.

The first flexible member may be prepared from any of a variety of materials, including but not limited to, natural and synthetic rubbers, either foamed or unfoamed. In a preferred embodiment, the first flexible member is of neoprene and has a thickness of about 0.174 inches to about 0.236 inches, a width of from about 1.5 inches to about 1.625 inches. Preferably, the first flexible member is stretchable to a limited degree, and has an elongation of about 20% to about 30%

Figure 2:
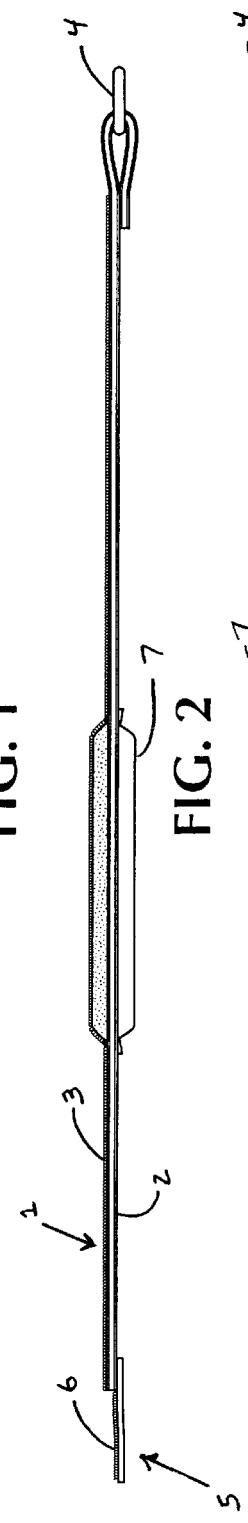
FIG. 2 is a side view of the knee strap of FIG. 1, showing the sewn-on fabric pouch that holds the tubular member on the bottom, and a projection of the tubular member against the fabric on the top. The top is shown with a hook-engagable material bonded thereto.
Figure 4:
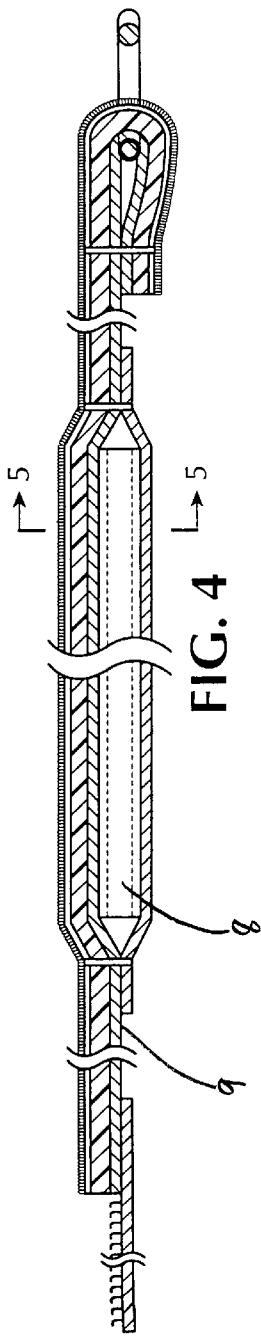
FIG. 4 is a cross-sectional view of the strap.

As shown on the bottom of FIG. 2, the knee strap is provided with a fabric pouch (7) which encloses and secures a compressible tubular member (8), such as, for example, a section of compressible rubber tubing. As shown in FIG. 4 an optional third fabric covering (9) may be secured to the bottom side of the strap, which may be formed of a suitable soft material or fabric, such as a soft nylon, polyester and spandex blend, a flannel or a persperation absorbing material, to provide for a comfortable feel against the human skin when the strap is applied to the human knee. The optional fabric (9) is optionally colored to add to the aesthetics of the knee strap.

Figure 3:
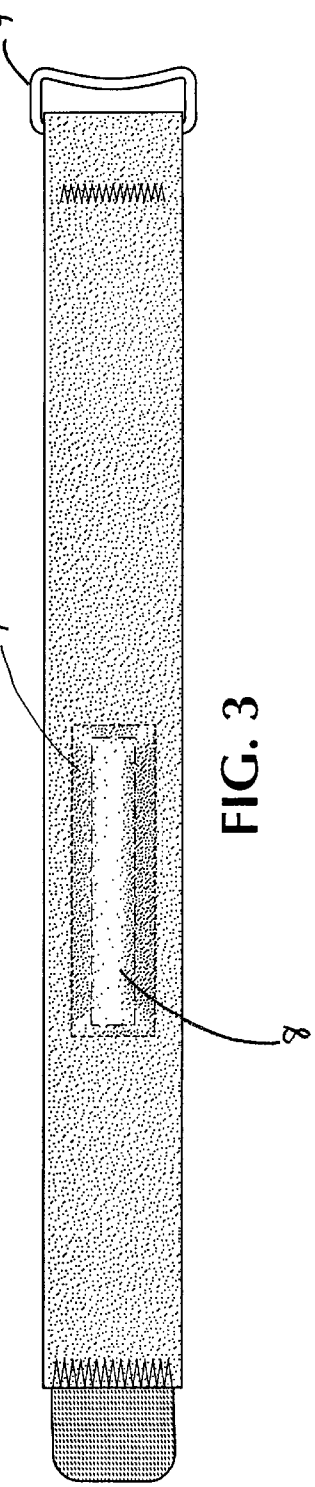
FIG. 3. is a top view of the knee strap of FIG. 1, with the hook-engagable material bonded thereto.

The compressible tubular member is held in place on the bottom side of the knee strap by a fabric pouch (7), which is sewn onto the knee strap, as shown in FIGS. 2 and 3; and in cross-section in FIG. 4.

Figure 7:
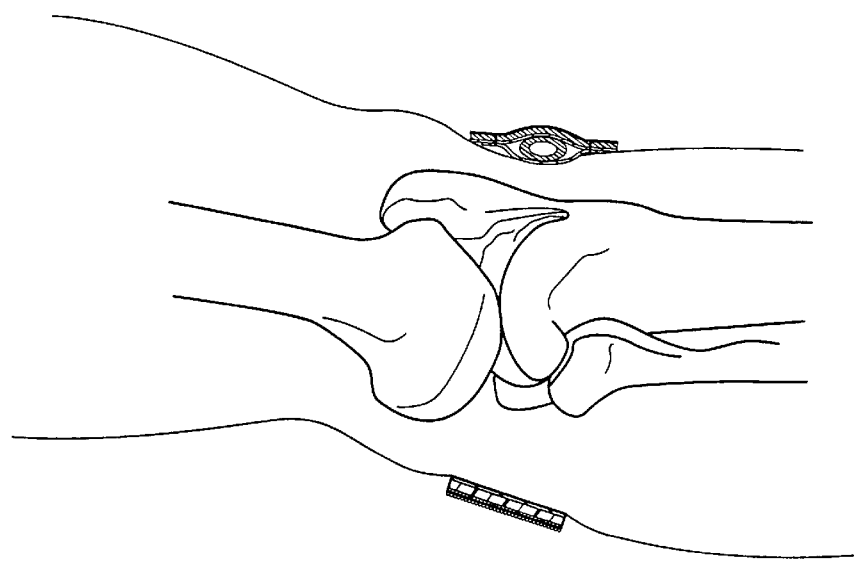
FIG. 7. is a cutaway view of the human knee of Fig.6, showing the placement of the knee strap relative to the patella.
Figure 6:
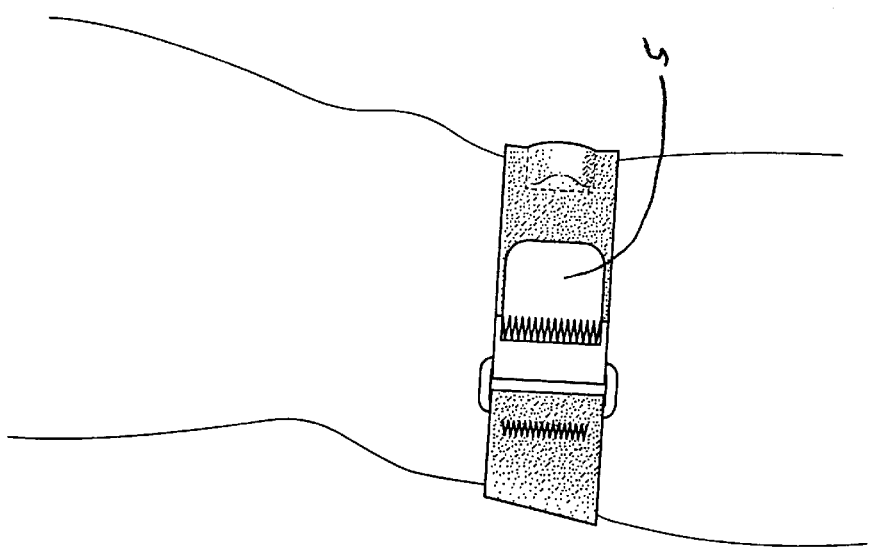
FIG. 6 is a view of the strap as installed on the knee of a human patient.
Figure 5:
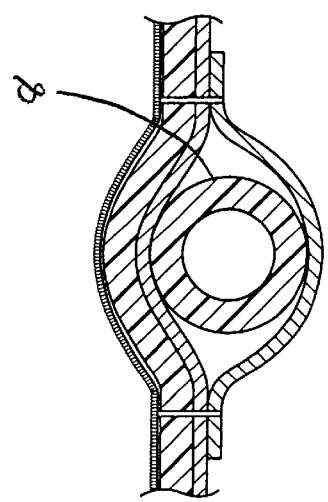
FIG. 5. is a sectional view of the strap of FIG. 4, showing the tubular member encased in the fabric pouch.

In use, the knee strap is applied to the knee with the compressible tubular member bearing against the front of the knee, and immediately beneath the patella, as shown in FIG. 6, and as also shown in the cutaway view of FIG. 7. The adjustable strap fasteners are oriented to the side of the knee, and not in front of or behind the knee, as shown in FIG. 6.

Knee strap 1 is comprised of an elongated first flexible fabric member 2 having bonded thereto an optional second (3) and optional third (9) flexible material. The length of the strap is generally from about 12 to about 19 inches. The length of the strap can, of course, be increased or decreased to accommodate larger or smaller individuals. The length of the strap must be sufficient to encircle the user's leg at a point immediately below the kneecap, i.e., the patella, as shown in FIGS. 6 and 7.

Figure 1:
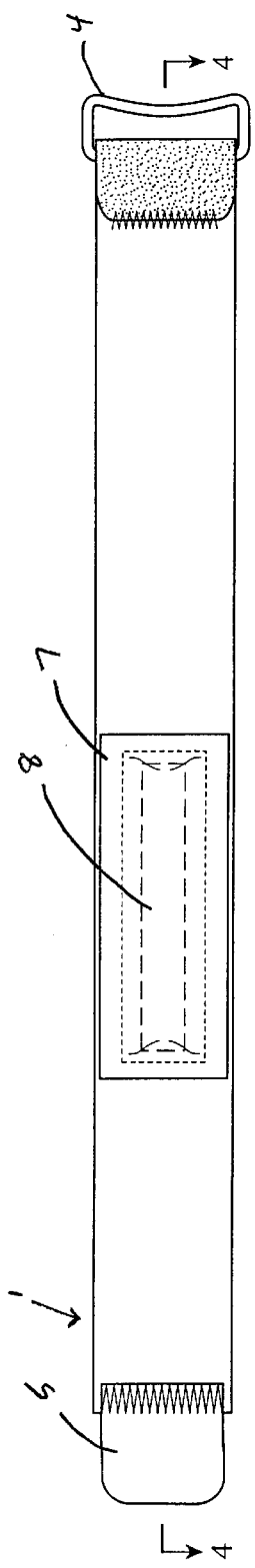
FIG. 1 is a bottom view of the knee strap (i.e., the side that comes into contact with the knee), showing stitching that passes through the strap and holds the pouch enclosing tubular member (8) to the bottom of the strap.

The Knee strap as shown in FIG. 1 is provided at a first end with a buckle (4), while the second end is adapted to be passed through the loop of the buckle on the first end, and then looped back upon itself to tighten the strap around the knee of the user, and the first end is also adapted to then be secured to prevent the strap from becoming loose. There are a variety of fasteners that can be used for the purpose, such as, for example, a common belt buckle at the first end and holes in the tongue at the second end which are engagable by a prong or wire in the conventional belt buckle; two-part snap connections, with one part being disposed on the tongue of the second end and the second part being disposed along the top surface of the strap; hook and loop fasteners where, as illustrated, the hook portion is attached to the tongue on the second end and is engagable with the material on the top surface of the strap; and the like; although hook and loop fasteners are preferred. The figures herein illustrate the strap with the preferred hook and loop fasteners.

In applying the strap illustrated in the figures to a human knee, the end portion having the tongue is inserted through the loop of the buckle at the other end, and pulled back over the top of the strap until the strap is tight. The hook portion of the hook and loop fastener which is attached to the tongue at the end of the strap is then engaged with the hook engagable material on the surface of the strap, which secures the strap in the tightened position. To remove the strap, the tongue is disengaged from the hook engagable material on the surface of the strap, and the end of the strap is then pulled back through the buckle to open the strap and remove it. The removable and adjustable fasteners, such as the complementary hook and hook engagable materials described, enable the strap to accommodate a wide range of sizes and the knee strap is, therefore, applicable to other uses, such as for providing support to an elbow or wrist.

In a preferred embodiment, the tubular member is a latex rubber tube and is about 3.25 inches long and has an outside diameter of about 0.375 inches. Preferably, the tubular member positioned along the length of the knee strap to enable the tubular member to bear on the front of a patient's knee while the buckle bears on the side of the knee. While one particular length will accommodate a wide variety of knee sizes, the length of the strap and the position of the tubular member along the length can be adjusted to accommodate any size knee. In the embodiment shown in FIG. 1, the strap is about 12 to about 19 inches long (measured from the end of the buckle to the tip of the tongue), and the tubular member is positioned about 4½ to 5 inches from the tip of the tongue, as measured from the tip of the tongue to the end of the tubular member closest to the tongue.

Although there are a variety of tubing materials which can be used for the tubular member of the present invention, and the degree of compression or softness of the tubings that can be used can vary, it is generally preferable that the tubing have a Durometer (Shore A) hardness of from about 30 to about 65.

The knee strap 1 of the present invention is installed on the knee of a human patient in the following manner. While sitting or standing with the knee straight (extended), the strap is positioned over the leg with the tubular member bearing against the front of the knee immediately beneath the kneecap. The two ends of the strap are wrapped around the leg so that the buckle is positioned to the side of the knee, not in front of or behind the knee, and the tongue end is passed through the buckle until the strap is securely tightened, and the tongue end is then fastened to prevent it from slipping back through the buckle, thereby holding the strap tight against the knee. As illustrated in FIG. 6, the tongue end is preferably fastened by a hook and loop fastener system.

While specific materials have been described above as preferred materials for manufacturing the present invention, it should be understood that other materials could be substituted therefor. For example, the hook and loop (or hook and hook engagable material) fastening system is the most convenient but could, of course, be replaced by other equivalent fastening arrangements.

While particular embodiments of the present invention have been illustrated and described, it would be obvious to those skilled in the art that various other changes and modifications can be made without departing from the spirit and scope of the invention.

We claim:

1. A knee strap comprising an elongated flexible member having a length sufficient to encircle a human patient's leg at a point immediately below the patella of said human patient's leg, said strap having a first end and a second end, a tubular member positioned on the strap in an orientation that is offset to the left or right of the midpoint of the length of the strap, and wherein the tubular member is encased within a cloth pouch affixed to one surface of the strap, at least one of said ends being provided with a fastener which is adjustably engagable with the other-end of the strap or with a surface of the strap to adjustably secure the strap around the side of a human patient's knee said tubular member having a length of about 3.25 inches, an outside diameter of about 0.375 inches and is positioned about 4½ to 5 inches from the tip of said other end.

2. The knee strap according to claim 1 wherein said tubular member is a compressible latex tube.

3. The knee strap according to claim 1 wherein said elongated flexible member is comprised of natural or synthetic rubber.

4. The knee strap according to claim 1 wherein said elongated flexible member has a top surface and a bottom surface, a hook engagable material is laminated to the top surface, said first end of said elongated flexible member is provided with a buckle having an opening sufficient to accommodate said second end, and said second end is provided with a tongue bearing a hook material which is engagable with the hook engagable material on said top surface of said elongated flexible member.

5. The knee strap according to claim 4 wherein said bottom surface is laminated to a fabric covering.

6. The knee strap of claim 5 wherein said fabric covering is a nylon/polyester/spadex blend.

7. The knee strap according to claim 1 having a length of from about 12 to about 18 inches.

* * * * *

UNITED STATES PATENT AND TRADEMARK OFFICE
CERTIFICATE OF CORRECTION

PATENT NO. : 6,485,448 B2
DATED : November 26, 2002
INVENTOR(S) : Cindy Lamping et al.

It is certified that error appears in the above-identified patent and that said Letters Patent is hereby corrected as shown below:

Column 6,
Line 26, change "spadex" to -- spandex --

Signed and Sealed this

Eighteenth Day of March, 2003

JAMES E. ROGAN
*Director of the United States Patent and Trademark Office*